(12) United States Patent
Ozcan et al.

(10) Patent No.: US 10,663,466 B2
(45) Date of Patent: May 26, 2020

(54) PORTABLE RAPID DIAGNOSTIC TEST READER AND METHODS OF USING THE SAME

(71) Applicant: THE REGENTS OF THE UNIVERSITY OF CALIFORNIA, Oakland, CA (US)

(72) Inventors: Aydogan Ozcan, Los Angeles, CA (US); Onur Mudanyali, Los Angeles, CA (US); Stoyan Dimitrov, Los Angeles, CA (US); Uzair Sikora, Harbor City, CA (US); Swati Padmanabhan, Los Angeles, CA (US); Isa Navrus, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1324 days.

(21) Appl. No.: 14/530,517

(22) Filed: Oct. 31, 2014

(65) Prior Publication Data

US 2015/0111201 A1 Apr. 23, 2015

Related U.S. Application Data

(62) Division of application No. 13/485,689, filed on May 31, 2012, now Pat. No. 8,916,390.
(Continued)

(51) Int. Cl.
*G01N 33/569* (2006.01)
*G06F 16/245* (2019.01)
(Continued)

(52) U.S. Cl.
CPC ....... *G01N 33/56905* (2013.01); *G01N 21/01* (2013.01); *G01N 21/645* (2013.01);
(Continued)

(58) Field of Classification Search
None
See application file for complete search history.

(56) References Cited

U.S. PATENT DOCUMENTS

| 5,104,512 A | 4/1992 | Gombocz et al. |
| 5,439,578 A | 8/1995 | Dovichi et al. |

(Continued)

FOREIGN PATENT DOCUMENTS

| EP | 1 710 565 A1 | 10/2006 |
| EP | 1710565 A1 | 11/2006 |

(Continued)

OTHER PUBLICATIONS

Mudanyali, Onur et al., Integrated rapid-diagnostic-test reader platform on a cellphone, Lab Chip, 2012, 12, 2678-2686.
(Continued)

*Primary Examiner* — Melanie Brown
*Assistant Examiner* — Richard Moerschell
(74) *Attorney, Agent, or Firm* — Vista IP Law Group LLP

(57) ABSTRACT

A portable rapid diagnostic test reader system includes a mobile phone having a camera and one or more processors contained within the mobile phone and a modular housing configured to mount to the mobile phone. The modular housing including a receptacle configured to receive a sample tray holding a rapid diagnostic test. At least one illumination source is disposed in the modular housing and located on one side of the rapid diagnostic test. An optical demagnifier is disposed in the modular housing interposed between the rapid diagnostic test and the mobile phone camera.

14 Claims, 11 Drawing Sheets

Related U.S. Application Data

(60) Provisional application No. 61/595,584, filed on Feb. 6, 2012, provisional application No. 61/623,212, filed on Apr. 12, 2012.

(51) Int. Cl.

| | |
|---|---|
| G01N 21/84 | (2006.01) |
| G01N 21/64 | (2006.01) |
| G16H 15/00 | (2018.01) |
| G06K 7/10 | (2006.01) |
| G01N 21/01 | (2006.01) |
| G01N 21/77 | (2006.01) |
| G01N 21/82 | (2006.01) |
| G01N 33/543 | (2006.01) |

(52) U.S. Cl.
CPC ..... *G01N 21/8483* (2013.01); *G01N 33/5695* (2013.01); *G01N 33/56988* (2013.01); *G06F 16/245* (2019.01); *G06K 7/10732* (2013.01); *G16H 15/00* (2018.01); *B01L 2300/0825* (2013.01); *G01N 33/543* (2013.01); *G01N 2021/0118* (2013.01); *G01N 2021/7786* (2013.01); *G01N 2021/825* (2013.01); *G01N 2021/8488* (2013.01); *G01N 2201/0221* (2013.01); *G01N 2201/062* (2013.01); *G01N 2201/0634* (2013.01); *G06K 7/10831* (2013.01); *Y02A 90/22* (2018.01); *Y02A 90/24* (2018.01); *Y02A 90/26* (2018.01)

(56) References Cited

U.S. PATENT DOCUMENTS

| | | | |
|---|---|---|---|
| 5,526,120 A | 6/1996 | Jina et al. | |
| 5,738,828 A | 4/1998 | Stoughton | |
| 6,542,905 B1* | 4/2003 | Fogel | G06F 19/327 |
| 6,602,191 B2 | 8/2003 | Quy | |
| 7,816,147 B2 | 10/2010 | Carpenter | |
| 9,053,222 B2* | 6/2015 | Lynn | G06F 19/321 |
| 2002/0160517 A1 | 10/2002 | Modzelewski et al. | |
| 2002/0192833 A1* | 12/2002 | Pan | G01N 21/8483 436/164 |
| 2003/0112432 A1 | 6/2003 | Yguerabide et al. | |
| 2003/0160958 A1* | 8/2003 | Yamauchi | G01N 21/8483 356/344 |
| 2003/0163351 A1* | 8/2003 | Brown | A61B 5/0002 705/2 |
| 2003/0169426 A1 | 9/2003 | Peterson et al. | |
| 2004/0211242 A1* | 10/2004 | Holmuhamedov | G01N 33/48728 73/23.2 |
| 2006/0142947 A1* | 6/2006 | Robrish | G01N 21/77 702/19 |
| 2006/0222567 A1 | 10/2006 | Kloepfer et al. | |
| 2006/0238858 A1* | 10/2006 | Kawasaki | G02B 21/025 359/368 |
| 2006/0240541 A1* | 10/2006 | Petruno | G01N 21/8483 435/287.2 |
| 2006/0246574 A1* | 11/2006 | Rosenstein | G01N 33/558 435/287.2 |
| 2008/0171397 A1* | 7/2008 | Hardcastle | G01N 21/253 422/52 |
| 2008/0287316 A1* | 11/2008 | Spivey | G01N 33/54366 506/12 |
| 2009/0292479 A1* | 11/2009 | Chuang | G01N 21/6452 702/19 |
| 2010/0175006 A1* | 7/2010 | Li | G06F 17/30672 715/764 |
| 2010/0254581 A1 | 10/2010 | Neeser et al. | |
| 2010/0315644 A1 | 12/2010 | Egan et al. | |
| 2011/0009163 A1 | 1/2011 | Fletcher et al. | |
| 2011/0019883 A1* | 1/2011 | Bremnes | G06K 7/14 382/128 |
| 2011/0119075 A1* | 5/2011 | Dhoble | G06F 19/3456 705/2 |
| 2011/0207137 A1 | 8/2011 | Malik et al. | |
| 2012/0002852 A1 | 1/2012 | Karasikov et al. | |
| 2012/0157160 A1 | 6/2012 | Ozcan et al. | |
| 2012/0188378 A1* | 7/2012 | Hsiao | G01N 21/274 348/161 |
| 2012/0218379 A1 | 8/2012 | Ozcan et al. | |
| 2012/0244624 A1* | 9/2012 | Hsiao | G01N 21/8483 436/86 |
| 2012/0248292 A1 | 10/2012 | Ozcan et al. | |
| 2013/0066563 A1* | 3/2013 | Hengstler | G16H 40/67 702/19 |
| 2013/0079599 A1* | 3/2013 | Holmes | G06F 19/366 600/300 |
| 2013/0092821 A1 | 4/2013 | Ozcan et al. | |
| 2013/0157351 A1 | 6/2013 | Ozcan et al. | |
| 2013/0244339 A1 | 9/2013 | Ehrenkranz et al. | |
| 2013/0258091 A1 | 10/2013 | Ozcan et al. | |
| 2013/0273528 A1 | 10/2013 | Ehrenkranz et al. | |
| 2013/0280752 A1 | 10/2013 | Ozcan et al. | |
| 2014/0120563 A1 | 5/2014 | Ozcan et al. | |
| 2014/0213468 A1 | 7/2014 | Ehrenkranz et al. | |

FOREIGN PATENT DOCUMENTS

| | | |
|---|---|---|
| JP | 2001-296246 | 10/2001 |
| JP | 2008 286522 A | 11/2008 |
| JP | 6139565 | 5/2017 |
| KR | 10-2005597 | 7/2019 |
| WO | WO 2006/106084 A1 | 10/2006 |
| WO | 2009/063185 A1 | 5/2009 |
| WO | WO 2009/063185 A1 | 5/2009 |
| WO | 2010/063304 A1 | 6/2010 |
| WO | 2010/095394 | 8/2010 |

OTHER PUBLICATIONS

Zhu, Hongying et al., Cost-effective and compact wide-field fluorescent imaging on a cell-phone, Lab Chip, 2011, 11, 315-322.

Office Action dated Mar. 22, 2016 in Japanese Application No. 2014-555540, including English translations prepared by Kita-Aoyama International Patent Bureau; Applicant: The Regents of the University of California (11pages).

Biener, Gabriel et al., Combined reflection and transmission microscope for telemedicine applications in field settings, DOI:10.1039/C1lc20169g, Accepted May 27, 2011, www.rsc.org/loc, Lab Chip, Aug. 21, 2011 11(16):2738-43, Epub Jun. 27, 2011 (8 pages).

Breslauer, David N. et al., Mobile Phone Based Clinical Microscopy for Golab Health Application, PLoS One | www.plosone.org, Jul. 2009, vol. 4, Issue 7, e6320 (7 pages).

Tuijn, Coosje et al., Data and Image Transfer Using Mobile Phones to Strengthen Microscopy-Based Diagnostic Services in Low and Middle Income Country Laboratories, PLoS One | www.plosone.org, Dec. 2011, vol. 6, Issue 12, e28348 (8 pages).

Roche, Philip J.R. et al., A Camera Phone Localised Surface Plasmon Biosensing Platform towards Low-Cost Label-Free Diagnostic Testing, DOI:10.1155/2011/406425, Hindawi Publishing Corporation, Journal of Sensors, vol. 2011, Article ID 406425 (7 pages).

Lee, Myungjun et al., Field-portable reflection and transmission microscopy based on lensless holography, Sep. 1, 2011, vol. 2, No. 9, Biomedical Optics Express, pp. 2721-2730.

Veratox for Peanut Allergen (1page) (undated).

Neogen Microplate Reader (6704) (1page) (undated).

Zhu, Hongying et al., Cost-effective and compact wide-field fluorescent imaging on a cell-phone, Lab on a Chip, Jan. 21, 2011, vol. 11, Issue 2, pp. 315-322.

PCT International Search Report for PCT/US2012/040282, Applicant: The Regents of the University of California, Form PCT/ISA/210 and 220, dated Dec. 28, 2012 (5pages).

PCT Written Opinion of the International Search Authority for PCT/US2012/040282, Applicant: The Regents of the University of California, Form PCT/ISA/237, dated Dec. 28, 2012 (6pages).

(56) References Cited

OTHER PUBLICATIONS

You, David J. et al., Direct and sensitive detection of foodborne pathogens within fresh produce samples using a field-deployable handheld device, Biosensors and Bioelectronics 28 (2011) 399-406.
PCT International Preliminary Report on Patentability (Chapter I of the Patent Cooperation Treaty) for PCT/US2012/040282, Applicant: The Regents of the University of California, Form PCT/IB/326 and 373, dated Aug. 21, 2014 (8pages).
Hardie et al., Joint MAP Registration and High-Resolution Image Estimation Using a Sequence of Undersampled Images, IEEE, vol. 6 No. 12, Dec. 1997.
Ozcan et al., Ultra wide-filed lens-free monitoring of cells on-chip, Lab on Chip 8, 89-106, Nov. 1, 2007.
Ozcan et al., Lens-free On-Chip Cytometry for wireless Health Diagnosis, IEEE LEOS Newsletter, Oct. 2008.
Seo et al., Lensfree On-chip Cytometry Using Tunable Monochromatic Illumination and Digital Noise Reduction, Multi-color LUCAS, Sep. 2008.
Seo et al., Lensfree holographic imaging for on-chip cytometry and diagnostics, Lab on a Chip, 9, 777-787, Dec. 5, 2008.
Su et al., Towards Wireless Health: Lensless On-Chip Cytometry, Biophotonics, Dec. 2008.
Su et al., High-Throughput Lensfree Imaging and Characterization of Heterogeneous Cell Solution On a Chip, Biotechnology and Bioengineering, Sep. 8, 2008.
Isikman et al., Lensfree Cell Holography On a Chip: From Holographic Cell Signatures to Microscopic Reconstruction, LEOS Annual Meeting Conf. Proceedings, Oct. 2009.
Mudanyali et al., Lensless On-chip Imaging of Cells Provides a New Tool for High-throughput Cell-Biology and Medical Diagostics, Journal of Visualized Experiments, Dec. 14, 2009.
Bishara et al., Lensfree on-chip microscopy over a wide field-of-view using pixel super-resolution, Optics Express, vol. 18 No. 11, May 24, 2010.
Coskun et al., Wide field-of-view lens-free fluorescent imaging on a chip, Lab Chip, 10(7), 824-827, Apr. 7, 2010.
Coskun et al., Lensless wide-field fluorescent imaging on a chip using compressive decoding of sparse objects, Optics Express, vol. 18 No. 10, May 5, 2010.
Khademhosseinieh et al., Lensfree color imaging on a nanostructured chip using compressive decoding, Applied Physics Letters, 97, 211112-1, Nov. 24, 2010.
Khademhosseinieh et al., Lensfree on-chip imaging using nanostructured surfaces, Applied Physics Letters, 96, 171106, Apr. 30, 2010.
Mudanyali et al., Compact, light-weight and cost-effective microscope based on lensless incoherent holography for telemedicine applications, Lab Chip, 10, 1417-1428, Apr. 19, 2010.
Ozcan, Smart technology for global access to healthcare, SPIE, Mar. 16, 2010.
Ozcan et al., Lensfree on-chip holography facilitates novel microscopy applications, SPIE, May 19, 2010.
Bishara et al., Holographic pixel super-resolution in portable lensless on-chip microscopy using a fiber-optic array, Lab on a Chip 11, 1276-1279, Mar. 1, 2011.
The Extended European Search Report dated Sep. 25, 2015 in European Application No. 12867945.3, Applicant: The Regents of the University of California, (13pages).
Communication pursuant to Article 94(3) EPC dated May 12, 2017 in European Patent Application No. 12867945.3-1554, (9pages).
Notice of Preliminary Rejection (non-final) dated Dec. 6, 2018 for Korean Patent Application No. 10-2014-7021712, (6 pages).

\* cited by examiner

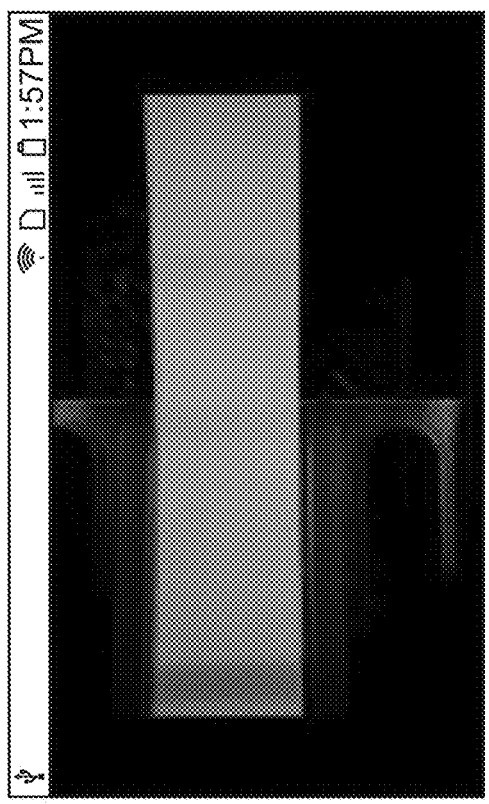
FIG. 7D
FIG. 7E
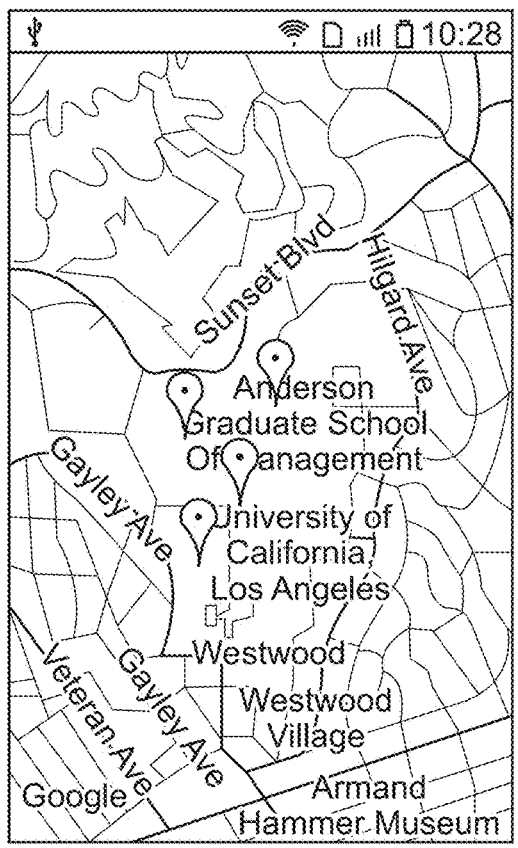
FIG. 7F
FIG. 7G

PORTABLE RAPID DIAGNOSTIC TEST READER AND METHODS OF USING THE SAME

RELATED APPLICATIONS

This Application is a divisional of U.S. patent application Ser. No. 13/485,689, filed on May 31, 2012, now U.S. Pat. No. 8,916,390, which claims priority to U.S. Provisional Patent Application No. 61/595,584 filed on Feb. 6, 2012 and U.S. Provisional Patent Application No. 61/623,212 filed on Apr. 12, 2012. Priority is claimed pursuant to 35 U.S.C. § 119 and 120 and any other applicable statutes. The above-noted Patent Applications are incorporated by reference as if set forth fully herein.

TECHNICAL FIELD

The field of the invention generally relates to devices and methods used in connection with rapid diagnostic tests (RDTs or RDT).

BACKGROUND

RDTs are diagnostic assays designed for use at the point-of-care. RDTs are generally low cost, relatively simple to operate and read, stable at a variety of operating conditions, and work in a relatively short period of time. Although the use of RDTs is not so limited, RDTs have particular application in low-resource settings where local conditions do not provide technology, equipment, and training for more complicated laboratory testing. Moreover, many patients may not reside near or cannot travel to medical sites where such testing is available.

RDTs are thus very useful tools to screen infectious diseases in resource limited settings or remote locations where conventional approaches (e.g., clinical examination, microscopy, etc.) are extremely limited or even not available. Penetration of RDT technologies to public health endeavors has generated several advantages including, but not limited to, better patient management where the infection symptoms are not specific to a particular disease (i.e., asymptomatic diseases), outbreak surveillance in high-risk endemic areas, and wide-spread health care delivery by minimally trained technicians.

A variety of types of RDTs are in existence. These include, by way of example, lateral flow tests (immunochromatographic strip tests), agglutination tests, flow-through tests, and solid-phase (dipstick) assays. Lateral flow tests are one of the most common types of RDT and include all the reactants and detection functionality included within a test strip. In a lateral flow test, the strip is placed into a sample and the results are read after a certain amount of time has elapsed. An example of a lateral flow test is commonly used home pregnancy tests. An agglutination RDT works by observing the binding of particles to a target analyte which is observed through the naked eye or through a microscope. In a solid phase RDT, a dipstick is placed into contact with a sample and then washed and incubated to prevent non-specific analyte blinding. This test requires several steps such as washing and thus requires some degree of training. These limitations can limit the usefulness of such tests in resource-limited settings. Flow through tests obtain results quicker than lateral flow tests but require buffer solutions and additional wash steps that can limit portability and usefulness.

RDTs are used to test for the presence of infectious disease. For example, RDTs are used to detect HIV, malaria, syphilis, and Hepatitis B. RDTs can also be used to detect other biomarkers or physical conditions. For example, RDTs are used in making fertility determinations. RDTs can also be used to test blood sugar and cholesterol levels.

Meanwhile, the current and expanding universe of wireless communication technology exhibits promising potential to be utilized for powerful wireless health applications even in the least developed parts of the world. With more than 5 billion subscriptions worldwide, mobile phones can be potentially used for sensing, screening and transferring ubiquitous health related data using already embedded components (i.e., CMOS/CCD sensors, LCD displays, WIFI/GSM/GPS receivers/transmitters, Bluetooth, etc.) even in field settings. Therefore, wireless communication technology remains an exciting opportunity to transform the fight against epidemics, opening new gates towards cloud-based outbreak monitoring platforms.

Attempts have been made at integrating mobile phones with diagnostic testing functionality. For example, Breslauer et al. have proposed a brightfield and fluorescent imaging system that includes a bulky attachment that is used in connection with a commercially available mobile phone. Breslauer et al., Mobile Phone Based Clinical Microscopy for Global Health Applications, PLOS One, www.plosone.org, Vol. 4, Issue 7 (2009). Smeared samples of malaria-infected cells and sickle cell anemia samples were imaged with the camera. These images were then transferred to a separate laptop computer for automated counting of cells. In another example, Tuijn et al. discloses a system whereby mobile phones are secured to a standard (and bulky) light microscope to capture images on a mobile phone. These images are then transferred to a central database for assessment, feedback, and educational purposes. Tuijn et al., Data and Image Transfer Using Mobile Phones to Strengthen Microscopy-Based Diagnostic Services in Low and Middle Income Country Laboratories, PLOS One, www.plosone.org, Vol. 6, Issue 12, (2011). Roche et al. have used a camera phone for applying localized surface plasmon resonance (LSPR) label-free sensing that uses gold nanoparticles and nanorods in an assay solution contained in a in a cuvette affixed to the mobile phone. Images obtained from the camera were then offloaded to a separate computer for image processing.

SUMMARY

In one embodiment, a portable rapid diagnostic test reader system includes a mobile phone having a camera and one or more processors contained within the mobile phone; a modular housing configured to mount to the mobile phone, the modular housing including a receptacle configured to receive a sample tray holding a rapid diagnostic test; at least one illumination source disposed in the modular housing and located on one side of the rapid diagnostic test; and an optical demagnifier disposed in the modular housing.

In one aspect of the invention a portable rapid diagnostic test reader system is provided that includes a mobile phone having a camera and one or more processors contained within the mobile phone. The test reader includes a modular housing configured to mount to the mobile phone, the modular housing including a receptacle configured to receive a sample tray holding a rapid diagnostic test. A first illumination source is disposed in the modular housing and located on a first side of the rapid diagnostic test while a second illumination source is disposed in the modular housing and located a second, opposing side of the rapid diagnostic test. An optical demagnifier is disposed in the modular housing. A switch is provided to selectively illuminate the rapid diagnostic test with either the first illumination source or the second illumination source.

In another embodiment, a method of reading a rapid diagnostic test using a mobile phone having camera functionality includes securing a rapid diagnostic test reader to the mobile phone. The rapid diagnostic test is inserted into the reader. The rapid diagnostic test is illuminated with illumination from one or more of the illumination sources. An image of the rapid diagnostic test is captured with the camera of the mobile phone. The captured image is processed with at least one processor and outputting a test result to the user based at least in part on the processed image.

A method of monitoring a pathological condition over an extended geographical area using RDT results obtained from a plurality of mobile phones includes receiving a plurality of RDT reports from the plurality of mobile phones at a computer that is remotely located from the plurality of mobile phones; storing the RDT reports in a database; receiving a query of the RDT reports contained in the database from a remote location; and returning query results to the remote location where the query is made.

BRIEF DESCRIPTION OF THE DRAWINGS

FIG. 7D illustrates a raw image of the RDT captured by the camera of the mobile phone.

FIG. 7E illustrates an exemplary diagnosis form that is presented to a user on a mobile phone. The diagnosis form indicates whether the test was valid or invalid and whether the test was positive or negative. The form also includes options for the user to provide user-specific information that will be associated with the test result.

FIG. 7F illustrates a map showing the location of several RDTs (e.g., positive tests) that is displayed to a user on a mobile phone.

FIG. 7G illustrates an antigen quantification screen that is displayed on a mobile phone device.

DETAILED DESCRIPTION OF THE ILLUSTRATED EMBODIMENTS

Figure 1A:
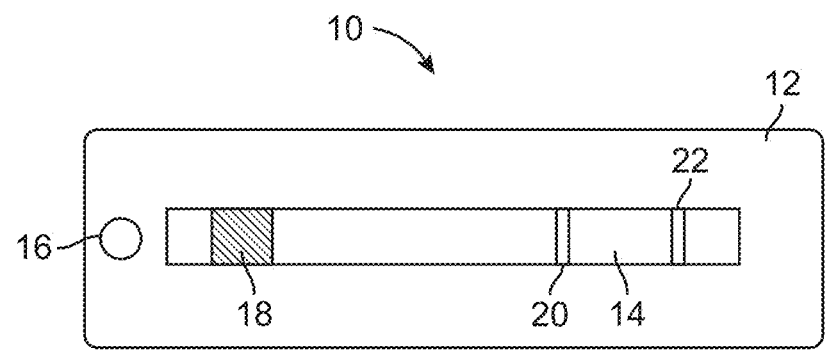
FIGS. 1A and 1B illustrate a view of an exemplary lateral flow RDT usable in connection with the test reader.
Figure 1B:
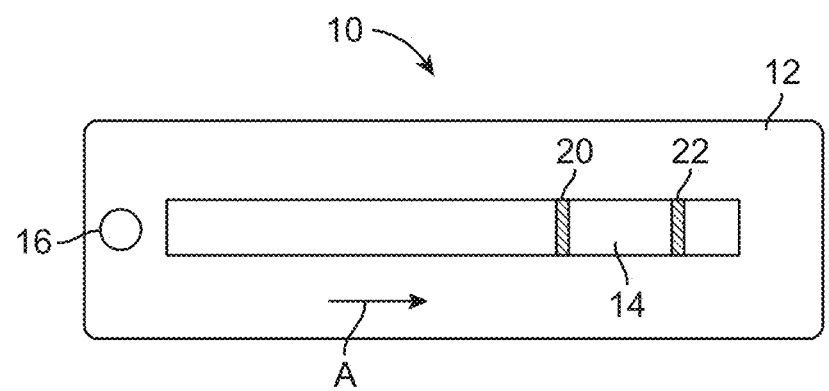

FIGS. 1A and 1B illustrate one type of rapid diagnostic test (RDT) 10. The RDT 10 illustrated in FIGS. 1A and 1B is a so-called lateral flow RDT 10 whereby capillary flow of liquid is used to move a sample and dye-labeled antibody specific to target antigen(s) across a substrate like a nitro-cellulose strip. The RDT 10 may include a housing 12 that is typically a rigid support substrate or holder that contains therein a test strip 14. The housing 12 may include one or more ports 16 into which a sample or other solutions are loaded into the RDT 10. The test strip 14 may include a nitro-cellulose strip that contains dye-labeled antibody 18 along a portion thereof that is carried down the length of the test strip 14 when a sample is loaded into the RDT 10. The dye-labeled antibody 18 may, in some embodiments, include one or more fluorescent dyes, molecules, or quantum dots making the RDT 10 a fluorescent RDT 10. The test strip 14 includes a test band 20 that typically consists of bound antibody bound to the test strip 14 along a thin test line. Also included on the test strip 14 is a control band 22 that includes bound antibody or antigen. It should be noted that in FIG. 1A, the test band 20 and the control band 22 are not normally visible prior to the depositing a sample on the RDT 10.

During use, a sample is loaded into the RDT 10, for example, by placing a sample in the port 16. The sample, may include any number of biological fluids including, for instance, blood, serum, plasma, sputum, and the like. The sample may even include other non-biological sources such as a water sample. After the sample has been loaded onto the RDT 10, the sample as well as the dye-labeled antibody 18 are drawn across the test strip 14 in the direction of arrow A. If the target antigen is present in the sample, some of the labeled antigen-antibody complex will be trapped on the test band 20. Excess labeled antibody is trapped on the control band 22. Often, colloidal gold is used to form gold-labeled antibody-antigen complexes that can then be visualized although the use of colloidal gold is not necessary with the concepts described herein.

While FIGS. 1A and 1B illustrate a test band 20 and a control band 22, the testing location and the control location may take other forms other than a band or line. For example, the testing location on the test strip 14 may take the form of a dot or other geometric shape. The same applies with respect to the control location on the test strip 14. Similarly, a single test strip 14 may contain multiple test sites and multiple control sites. For example, a single test strip 14 may test for the presence of multiple antigens. FIGS. 1A and 1B illustrate one type of RDT 10 that is usable in connection with the test reader described herein but it should be understood that other types of RDTs 10 may be useable in connection with the test reader. These include other formats like dipsticks, cassettes, strips, cards, pads or the like. Moreover, the test reader is usable with various RDT formats beyond lateral flow RDTs such as, for example, agglutination tests, flow-through tests, and solid-phase (dipstick) assays. What is common amongst all these different types of RDT formats is that there is a test location and control location that is capable of spectrographic interrogation and visualization.

Figure 2A:
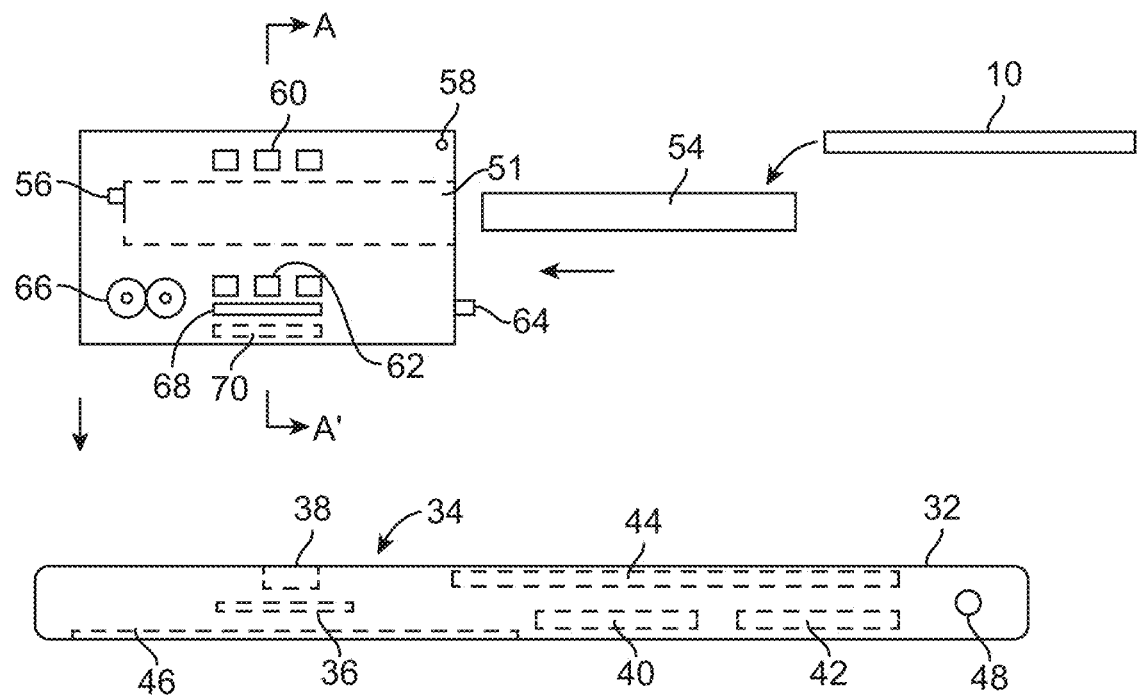
FIG. 2A is a side schematic representation of a portable RDT reader system according to one embodiment.

FIG. 2A schematically illustrates, in exploded format, a portable rapid diagnostic test reader system 30 according to one embodiment. The system 30 includes a mobile phone 32 that includes a camera 34 therein. In this regard, the camera 34 of the mobile phone 32 typically includes an imaging sensor 36 and a lens 38. The mobile phone 32 includes therein one or more processors 40 that are used to run software of the mobile phone 32 as well as communicate voice and data wirelessly to base stations (not shown) as part of a communications network. As described in more detail below, the processor(s) 40 of the mobile phone 32 are utilized, in one embodiment, to process and analyze captured images from the test reader. Thus, in this embodiment, the mobile phone 32 includes software loaded thereon for image processing. This software may be loaded in the memory (not illustrated) in the mobile phone 32 and may appear on the mobile phone 32 as an application or "app" which can then be run during testing. The application may be usable with a wide variety of operating systems including, but not limited to, ANDROID and IPHONE, operating systems. This software is executed or otherwise run on the processor(s) 40 of the mobile phone 32. In other embodiments, as explained below, image processing may take place in a remote location away from the mobile phone 32.

The mobile phone 32 may also include global positioning satellite (GPS) functionality for location-based services. GPS may be integrated into the processor(s) 40 described above or may be implemented with a dedicated GPS processor 42 or as integrated as part of the radiofrequency electronics of the mobile phone 32. The mobile phone 32 includes a battery 44, which in certain embodiments, is used to power the test reader as explained in detail below. The mobile phone 32 includes a display 46 that displays information to the user. These may be prompts and input fields for the user running the rapid diagnostic test or they may include test result information, image data, epidemiology information, geographical information, and the like. The mobile phone 32 illustrated in FIG. 2A includes an audio jack 48. In one embodiment, the audio jack 48 may be used as a switch to modulate between a transmission mode and a reflective mode for the test reader. The system 30 described herein is usable with any number of mobile phones 32 from any number of manufacturers (e.g., SAMSUNG, HTC, APPLE, NOKIA, MOTOROLA, and the like). These include so-called "smart phones" that generally have more features and functionality (and higher cost) than other mobile phones 32 as well as mobile phones 32 with less features. All that is required, is the ability of the mobile phone 32 to have camera functionality and communicate wirelessly over a network (e.g., GSM, CDMA, WiFi, Bluetooth, and the like). In this regard, in some embodiments, the mobile phone 32 may actually be more of a portable electronic device as opposed to a phone. For example, a portable electronic device that has camera functionality along with the ability to communicate wirelessly over a WiFi network can carry out many of the aspects described herein.

Figure 2B:
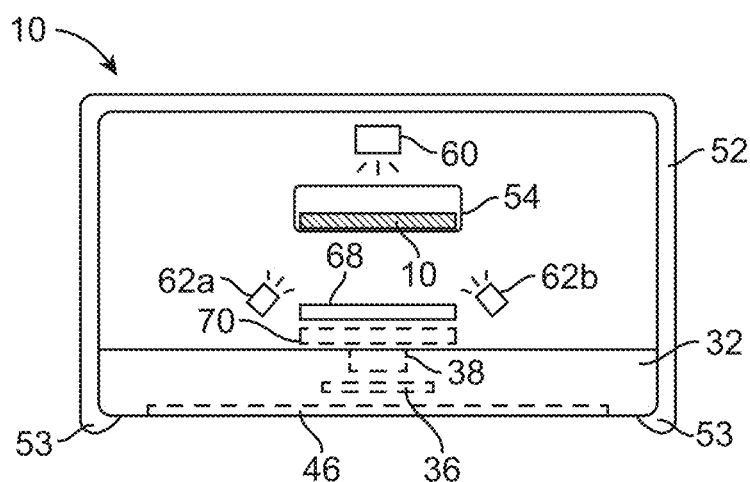
FIG. 2B is a cross-sectional view taken along the line A-A' with the sample tray and RDT loaded into the test reader.

Still referring to FIG. 2A, the system 30 includes a RDT test reader 50 that is configured to be removably attached to the mobile phone 32. The test reader 50 is generally compact such that when secured to the mobile phone 32, the combined apparatus is still hand-held. Generally, the test reader 50 has volume of less than about 500 $cm^3$ and weighs less than 300 grams (excluding batteries). The test reader 50 is configured to detachably mount to the face of the mobile phone 32 having the camera 34 thereon. As explained herein, the test reader includes a housing 52 that includes one or more contact points that engage with the outer body of the mobile phone 32 thereby allowing the test reader 50 to be affixed to the mobile phone 32. For example, the housing 52 may configured to engage the outer edges of the mobile phone 32 using tabs 53 (as seen in FIG. 2B) that flexibly engage the mobile phone 32. The housing 52 may have any number of geometries and configurations such that the test reader 50 can be attached to a wide variety of makes and models of mobile phones 32. The housing 52 is able to secure to the mobile phone 32 and substantially blocks out ambient light. Thus, rather than capturing images of RDTs 10 using room light or sunlight, the housing 52 includes its own illumination sources as described herein. Moreover, the housing 52 can be accurately placed on the mobile phone 32 to provide a uniform optical path between the illumination sources and the mobile phone camera 34. This increases measurement repeatability and voids reading errors due to illumination and field-of-view variations or tilts, all of which are substantially eliminated with the designs disclosed herein.

The test reader 50 includes a sample tray 54 that is dimensioned to hold a RDT 10 therein. The sample tray 54 may be dimensioned or otherwise configured with a particular RDT 10. For example, a sample tray 54 of a first type may be used to hold a RDT 10 for malaria from manufacturer ABC. A second, different sample tray 54 of a second type may be used to hold a RDT 10 for malaria from a different manufacturer. In this regard, the test reader 50 may be provided, in some embodiments, with a variety of different sample trays 54 with different sample trays 54 designed to hold different RDTs 10. For example, a kit may be provided that includes a test reader 50, multiple different sample trays 54, as well as instructions for use. The outer dimensions of the sample tray 54 are generally uniform across different RDTs 10 thus permitting the different sample trays 54 to be universally used in the same test reader 50. The sample tray 54 is configured to be inserted (in direction of arrow A) into the housing 52 of the test reader 50. The housing 52 may include a receptacle 51 therein that is dimensioned to hold the sample tray 54 at a fixed location therein such that the relevant portions of the RDT 10 can be imaged by the camera 34 of the mobile phone 32. The sample tray 54 may be reusable or, in other embodiments, may be disposable.

In one optional aspect, the housing 52 of the test reader 50 includes a position sensor 56 that is able to detect when the sample tray 54 has been properly inserted into the housing 52. For example, the sensor 56 may lock-out or prevent the illumination sources (described below) from actuating until the sample tray 54 has been properly inserted. Alternatively, the sensor 56 may be coupled to an indicator 58 such as a light or the like that indicates to the user that the sample tray 54 has been properly inserted into the test reader 50.

Still referring to FIG. 2A, the test reader 50 includes a first illumination source 60 that is disposed in the housing 52 so as to place the illumination source 60 on one side of the RDT 10. The first illumination source 60 is used as a transmission light source whereby light passes through the testing location of the RDT 10 (e.g., test strip 14). The first illumination source 60 may include one or more LEDs. In one particular embodiment, the first illumination source 60 may include an array of diffused LEDs (e.g., 754-1185-5-ND, Digi-key, USA). The test reader 50 further includes a second illumination source 62 that is located on an opposing side of the RDT 10 when loaded within the test reader 50. The second illumination source 62 is used as a reflection light source whereby light reflects off the testing location of the RDT 10. In one aspect, the second illumination source 62 includes first and second diffused LED arrays 62a, 62b (as seen in FIG. 2B) that are located underneath the plane of the RDT 10. As seen in FIG. 2B, the first diffused LED array 62a and the second diffused LED array 62b are angled and located outside the optical path to the camera 34 to ensure uniform illumination of the target test site. The particular wavelength of the first illumination source 60 and the second illumination source 62 can be tuned to best match the appropriate RDT 10. For example, it has been experimentally determined that LEDs with a peak wavelength of 565 nm achieves high contrast for both control and test lines for malaria RDTs that utilize colloidal gold. Of course, the illumination wavelength can be changed or tuned depending on the particular RDT 10. In one aspect, the test reader 50 may include the ability to modulate or adjust the particular wavelength(s) of light emitted from the first and second illumination sources 60, 62.

Reflection mode is practical and useful for most test formats including cassette-type RDTs 10 which have a plastic housing protecting a lateral flow pad with a window on one side as well as strip tests without any protective housing. Transmission mode is useful for strip-based RDTs 10. In order to give the user flexibility on whether to image in transmission or reflection mode a switch 64 is provided that toggles between transmission mode and reflection mode. In transmission mode, only the first illumination source 60 is activated during imaging. In reflection mode, only the second illumination source 62 is activated during imaging. In an alternative embodiment, instead of placing the switch 64 on the housing 52, the switch may be inserted into the audio jack 48 of the mobile phone 32.

In an alternative embodiment, the test reader 50 may only have one illumination source with no switching functionality. For example, the test reader 50 may include only the first illumination source 60 such that it operates exclusively in a transmission mode. Alternatively, the test reader 50 may have only the second illumination source 62 such that it operates exclusively in reflection mode.

Figure 4A:
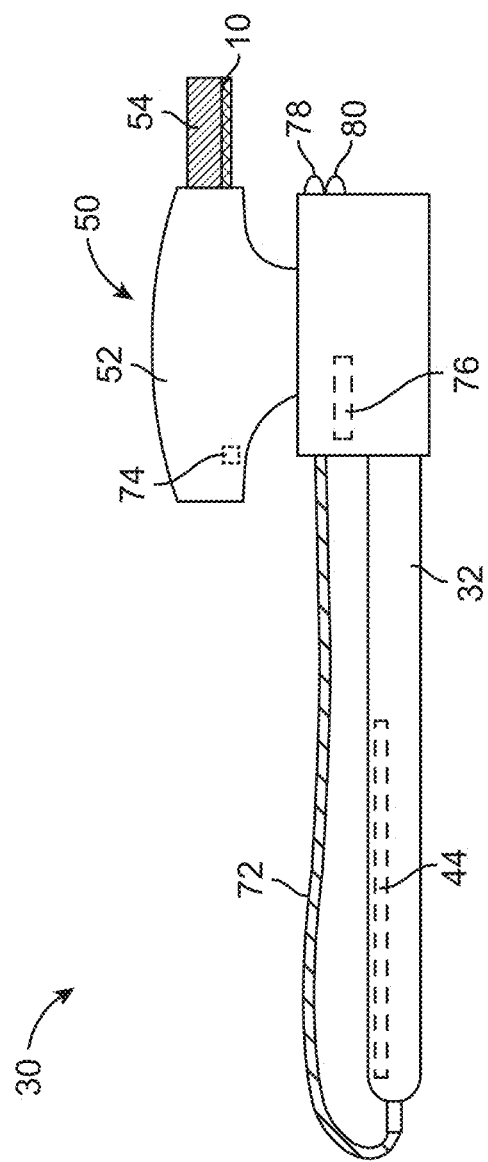
FIG. 4A is a side view of a portable RDT reader system according to another embodiment.
Figure 4B:
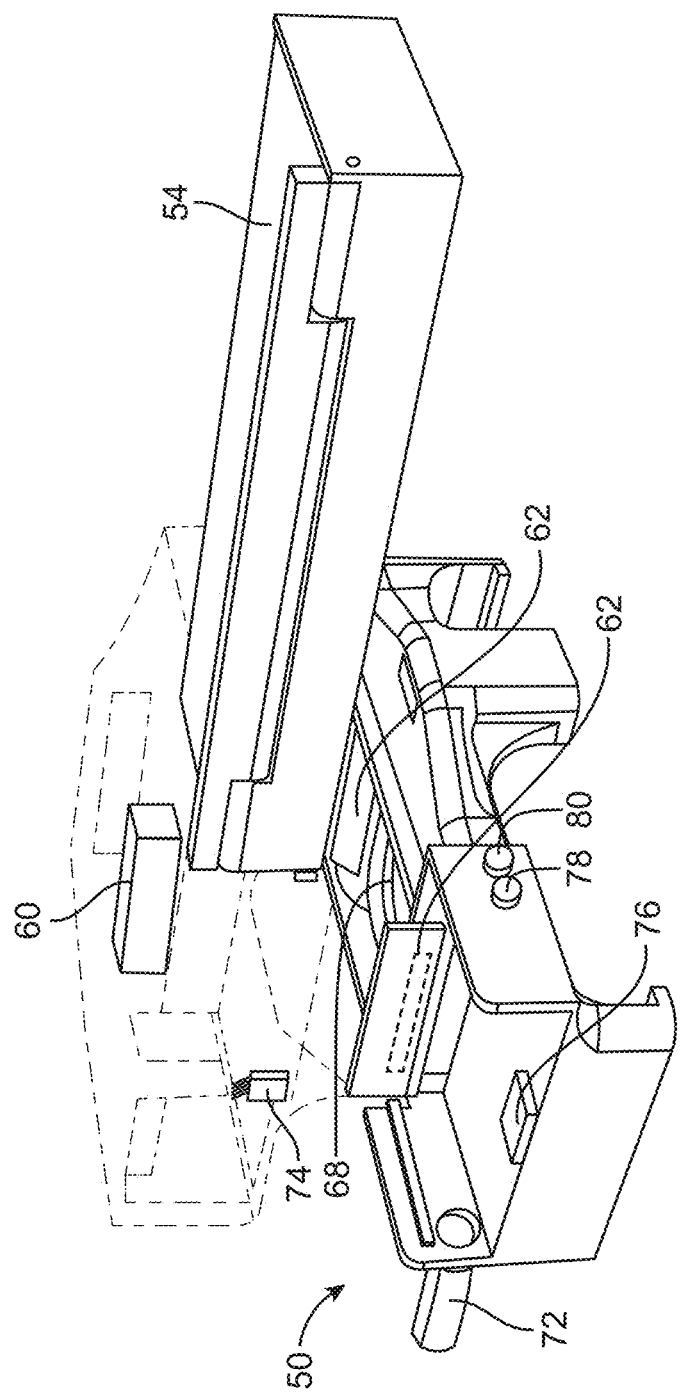
FIG. 4B is a partial perspective view of another embodiment of a RDT reader with portions of the housing removed so as to illustrate various interior components of the RDT reader.

To power the test reader 50, a battery 66 is provided in the housing 52. The test reader 50 does not have significant power requirements and may be powered by two AAA batteries although other battery types are also contemplated. In another embodiment, as illustrated in FIGS. 4A and 4B, rather than using one or more batteries 66, the battery 44 of the mobile phone 32 is used to power first and second illumination sources 60, 62, respectively. In this embodiment, a USB dongle or cable 72 connects the mobile phone 32 to the test reader 50 to provide power.

Referring to FIGS. 2A and 2B, the test reader 50 includes an optical demagnifier 68 that is used to demagnify the image. Rather than magnifying the area that is to be imaged, the test reader 50 needs to see a larger field of view. For this reason, an optical demagnifier 68 is interposed between the test plane of the RDT 10 and the camera 34 of the mobile phone 32. In one aspect, the optical demagnifier 68 is a lens (e.g., plano-convex lens with a focal length of less than about 20 mm). The optical demagnifier 68 has a demagnification factor that is within the range of between about 1 and about 50.

This demagnification factor can be tuned, if needed, by changing the focal length of the external lens of the test reader 50. Note that for digital image processing of the RDT results on the mobile phone 32, this optical demagnification factor together with the pixel size of the CMOS imager (e.g., ~1-2 μm) are the key factors to effect spatial sampling of RDT test lines. As expected, the overall magnification of the system, which also depends on the mobile phone 32 display size is not relevant for automated analysis of RDT results.

With reference to FIGS. 2A and 2B, in one alternative embodiment, the test reader 50 includes an optional color filter 70. The color filter 70 may be used for fluorescent RDTs 10. In this embodiment, one or both of the first illumination source 60 and/or the second illumination source 62 can be used as fluorescent excitation sources. The optional color filter 70 is used to reject the excitation light provided by these sources but permit the passage of the emitted fluorescent light such that it can then be read by the camera 34 on the mobile phone 32. The color filter 70 may be optionally removable from the housing 52 of the test reader 50. In this regard, the test reader 50 can be used with both fluorescent and non-fluorescent RDTs 10.

Figure 3:
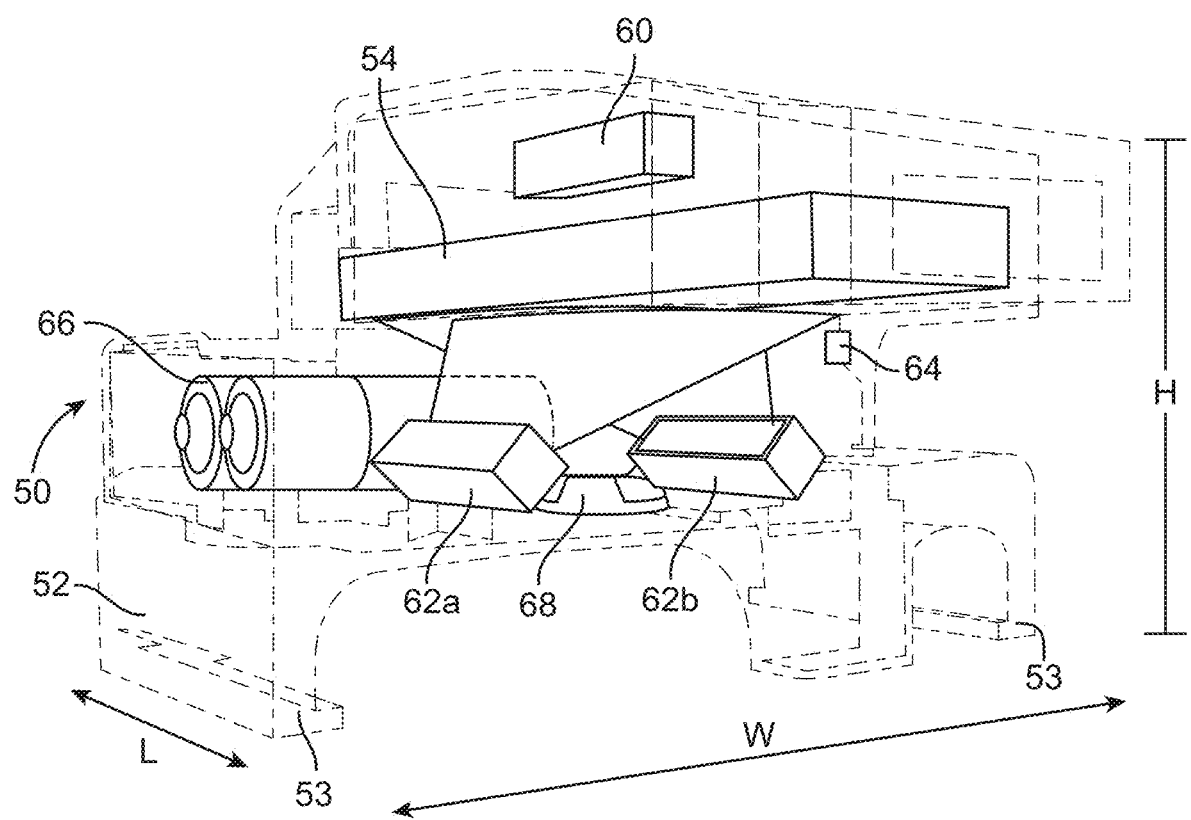
FIG. 3 is a partial perspective view of one embodiment of a RDT reader with portions of the housing removed so as to illustrate various interior components of the RDT reader.

FIG. 3 reveals a perspective view of a test reader 50 according to one embodiment. The test reader 50 is similar to that illustrated in FIGS. 2A and 2B. The test reader 50 of FIG. 3 is light-weight, weighing around 65 grams (excluding batteries). The width (W) of the test reader 50 is less than about 80 mm and has a length (L) of less than about 40 mm. The height (H) of the test reader 50 is less than about 50 mm. Of course, dimensions outside the ranges specifically mentioned above are nonetheless contemplated to fall within the scope of the invention provided the unit remains hand-held. The housing 52 may be made from a polymer material giving the same structural integrity while at the same time imparting some flexibility to the tabs 53 or other affixation points (e.g., tabs 53) so that the test reader 50 can be secured to the mobile phone 32 (now shown in FIG. 3).

FIGS. 4A-4B illustrate another embodiment of a portable rapid diagnostic test reader system 30. In this embodiment, a cable 72 such as a USB cable connects the mobile phone 32 to the test reader 50. In this way, the battery 44 from the mobile phone 32 is used to power all functionality of the test reader 50. Power is transmitted through the cable 72 and powers the first illumination source 60 and the second illumination source 62 (seen in FIG. 4B). In addition, in this embodiment, a tray sensor 74 is disposed in the housing 52 of the test reader 50 to detect whether the sample tray 54 containing the RDT 10 is properly loaded into the test reader 50 and ready to be imaged. This embodiment also uses a low cost processor 76 (e.g., micro-controller) that interfaces with the tray sensor 74 and controls two (2) visual indicators 78,

80 to alert the user that (i) the sample tray 54 is properly loaded into the test reader 50 and ready to be imaged and (ii) whether the test reader 50 is properly powered through the battery 44 of the mobile phone 32.

FIG. 4B illustrates a perspective view of the test reader 50 with various surfaces in phantom or removed so as to show various internal components of the test reader. FIG. 4B illustrates the first illumination source 60 used for testing the RDT 10 in the transmission mode. Also illustrated is the second illumination source 62, which may again be formed from two separate LED arrays, located on an opposing side of the sample tray 54. The second illumination source 62 is used for reflection mode testing. FIG. 4B illustrates an optical demagnifier 68 in the form of a lens disposed in the housing 52 of the test reader 50.

Figure 5:
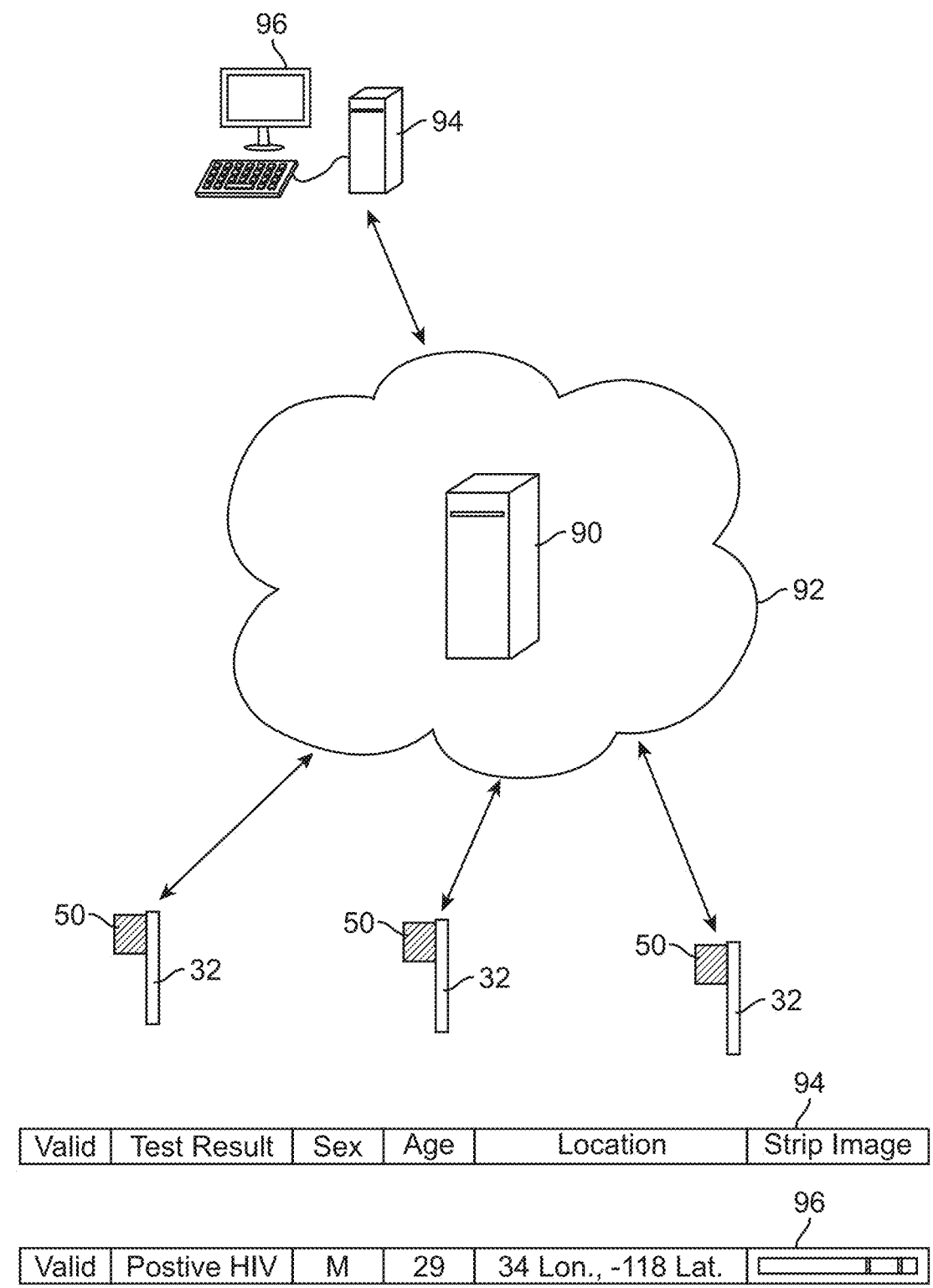
FIG. 5 is a schematic representation of a system that integrates multiple portable RDT readers.

As stated above, the mobile phone 32 contains a software application that digitally records images of the RDT 10 and, in one embodiment, rapidly evaluates the test results. The software application is executed, in one embodiment, using the one or more processors 40 contained in the mobile phone 32. Preferably, test results can be obtained within a short period of time such as within a few seconds. Once the image is captured using the test reader 50 attached to the mobile phone 32, the application stored on the mobile phone 32 then processes the image to generate a test result to the user. The test result includes at least two pieces of information: (1) a determination whether the test is valid or invalid, and (2) a determination whether the test is positive or negative. Optionally, a test report which includes additional information may also be generated by the application. The test report includes test result information in addition to information such as, patient-specific information (e.g., age, sex, medical history information), time-stamp, geographic location of where test conducted, geographic location of where tested individual is located, test image, disease type, (e.g., identification of disease), and test type data (e.g., manufacturer of test and other information). Geographic location may be automatically determined based on GPS locations generated, for example, by the GPS processor 42. Time-stamp data may be obtained using the date and time of the mobile phone 32 or the network on which such device runs. Using the wireless functionality of the mobile phone 32 (or other mobile electronic device), the same application that generates the test result and/or test report uploads the data to a remote server 90 that contains a database of plurality of test results of different users as illustrated in FIG. 5. A variety of different wireless protocols may be used to transmit the data including WiFi, GSM, CDMA, and the like. The data is transmitted across a network 92 that may include a proprietary network or an open network such as the Internet. The amount of data that is transferred is typically fairly low and is generally less than about 0.05 Mbytes per test. Data may also be transferred using the Short Message Service (SMS) functionality of the mobile phone 32. The application running on the mobile phone 32 may temporality store the test result on the mobile phone 32 if, for example, there is not sufficient wireless coverage or connection to the remote server 90 has been interrupted. The data can then be transmitted automatically to the remote server 90 once the connection has been re-established or manually transmitted by the user.

Still referring to FIG. 5, in one aspect, a personal computer 94 is able to access the database contained in the remote server 90. Using a standard web interface, a user of the personal computer 94 can query the database of the remote server 90 and display RDT data in a variety of different formats. For example, the user may display RDT data that is overlaid on top of a map. In such a case the display 96 of the personal computer 94 may illustrate a map of a particular geographic region with all the positive RDTs being displayed on the map at their respective geographical locations. This feature may be particularly use from an epidemiological standpoint such that disease progression and outbreaks can be monitored remotely. For example, the system 30 described herein may be used to develop and monitor a real-time infection map that shows the location of persons infected with a particular disease.

By having multiple mobile phones 32 equipped or otherwise used in connection with test readers 50 that communicate with a central database on a remote server 90, infectious diseases can be monitored and tracked across an extended geographical area. RDT results obtained from a plurality of mobile phones where they are transmitted and received at the remote server 90. Test reports received at the remote server 90 are stored in a database. The remote server 90 can then receive queries—either from the mobile phones 32 or from other computers connected to the remote server. Query results are returned to the remote location where the query is made.

In addition, the user can selectively filter data from the remote server 90 to display only the results of interest. For example, a user can filter based on a variety of attributes including disease type, test location, date, time, RDT type/manufacturer, patient age, sex, and the like. While FIG. 5 illustrates both personal computers 94 and mobile phones 32 that can access and query the database of the remote server 90 it should be understood that other electronic devices having web browser functionality may also be used for this purpose.

FIG. 5 illustrates an exemplary data header 94 of an example data packet that is transmitted from the mobile phone 32 to the remote server 90 over a network 92. The data header 94 may include determination of valid or invalid test; test result (i.e., positive or negative), sex, age, location (e.g., longitudinal and latitude coordinates), test type date, and strip image data. FIG. 5 also illustrates an example of a data packet 96 that is transmitted from the mobile phone 32 over the network 92 to the remote server 90. In this example, the data packet 96 concerns a valid test from a male subject age 29 that tested positive for the HIV virus. The data packet 96 further includes location data (longitude and latitude coordinates) and an image of the strip. It should be understood that the data packet 96 is exemplary and more or less information may be contained in the same.

The RDT images that are uploaded to the remote server 90 can also serve to identify possible duplicate uploads of the same test. This is done by examining the pixel values of the uploaded images. Once identified as the same test image, duplicate entries can be deleted or merged at the server side by, for example, an authorized superuser/root.

Figure 6:
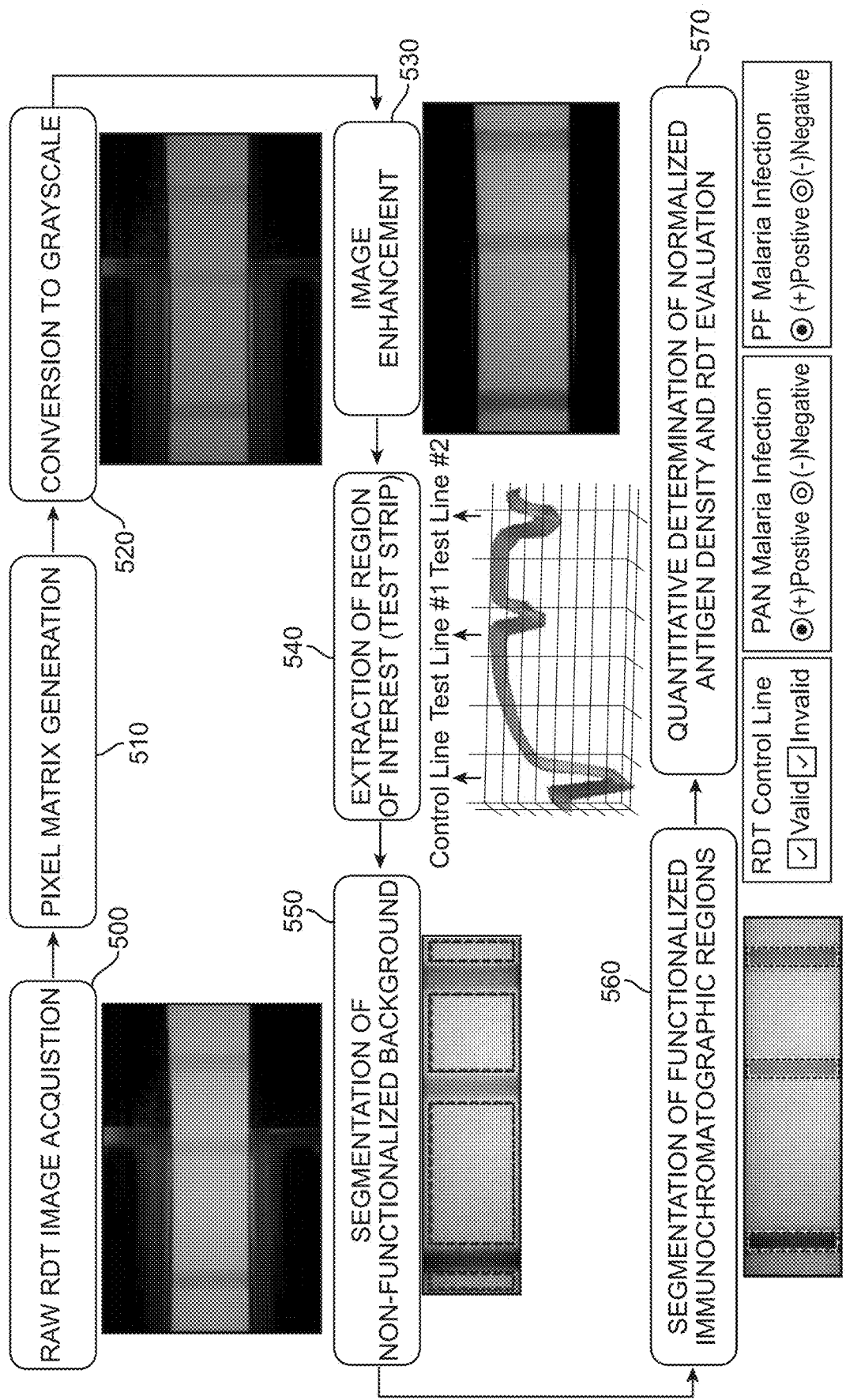
FIG. 6 illustrates an exemplary automated image analysis process for determining whether a RDT is valid/invalid and positive/negative.

With reference now to FIG. 6, the software stored on the mobile phone 32 automatically processes the raw images obtained of the RDT 10 using the system 30. The images may be obtained either in transmission mode or reflection mode. In operation 500, raw images are acquired using the camera 34. One such image is illustrated just adjacent to operation 500. These raw images obtained in operation 500 are then subject to pixel matrix generation in operation 510 wherein the image is then converted from 3 channel YUV420 scale to grayscale as seen in operation 520. The grayscale image is seen just below operation 520. In the images seen in FIG. 6, there are three (3) lines or bands appearing in the images. One line (the left most) in FIG. 6 represents the control line while the remaining two lines of FIG. 6 represent test lines. After the conversion to grayscale in operation 520, the image is enhanced in operation 530. All (3) three lines thus appear with greater clarity. In the next operation 540, the region(s) of interest are then extracted from the test strip 14. For example, as seen in the graph in operation 540 the three main regions of interest correspond to the image portions revealing the control line and two test lines. Extraction of the region(s) of interest can be accomplished by segmentation of the non-functionalized background as seen in operation 550. In this operation, the "background" portions of the image are identified. Correspondingly, segmentation of the functionalized immunochromatographic regions (i.e., the control and test regions) are identified as seen in operation 560. For example, initially the boundaries of the RDT lateral flow area are found, and the flow area is clipped out from the rest of the image.

Once the control and test regions are isolated and extracted, a quantitative determination is made of the RDT test evaluation to determine whether the test is valid or invalid as seen in operation 570. This is made be evaluating the extracted image region corresponding to the control region and comparing or thresholding this region to determine whether the RDT 10 is valid or invalid. Similarly, the extracted image regions corresponding to the test lines or test bands are compared or thresholded to determine whether the particular sample tested was positive or negative. In the example of FIG. 5, the sample was tested for PAN malaria infection and PF malaria infection. Both test lines are such that a positive determination is mode for both antigen types. While FIG. 6 illustrates one illustrative manner of image processing, it should be understood that other image processing algorithms and processes could be used to achieve the same result. A person of ordinary skill in the art could use a variety of different image processing techniques to isolate and evaluate the control and test lines that appear in raw images obtained from the camera 34 of the mobile phone 32.

In one particular embodiment, after the boundaries of the RDT 10 flow area are found and clipped out from the rest of the image, the average column pixel intensity per row is obtained, such that if the original grayscale image is a [R, C] matrix, one ends up with a [R, 1] column vector, with each element in the vector being the average value of the pixels in the corresponding row of the grayscale (single channel) image. Next, in the case of Optimal-IT Malaria RDT, the maximum value of the average column pixel intensity per row vector is taken and every pixel that is less than 90% of this value is zeroed in order to remove the parts of the image which do not carry any useful information such as the background. This leaves one with only non-zero values for pixels that are part of the RDT test strip 14 itself. The original grayscale image is taken and cropped by a rectangle that starts and ends at the rows where the threshold vector is non-zero. The strip stretches across the entire width of the image, so that the cropped rectangle has an equal amount of columns as the acquired image. The image is then saved to the private file-space of the mobile phone 32, to be uploaded to a server for data mining.

In the case of the CTK TB (Tuberculosis) and HIV RDTs (HIV 1/2 Ab PLUS Combo Rapid Tests and TBIgG/IgM Combo Rapid Tests, CTK Biotech Inc., CA, USA), the [R,1] average column pixel intensity per row vector is obtained from the image after first discarding 20% of the columns taken from both ends to avoid spatial artifacts. Then, the absolute value of the derivative of the average column pixel intensity per row vector is calculated to locate the rows that the strip lies on. Because of the acceleration in pixel values as one goes down the rows of the image, they occur right before and right after the target flow area. The original grayscale image is then digitally cropped across the appropriate rows, and finally saved to the private file-space of the mobile phone 32, to later be uploaded to a server for data mining.

Once the flow areas of the RDTs 10 are obtained, they are processed to get the locations of the control and infection lines. This is done by first creating a row vector obtained by averaging the pixel values along the columns of the image of flow areas. The local maxima of the row vector indicate the positions of the lines. To better handle detection noise and spatial non-uniformities on the RDT 10, a central moving averaging operation is also performed on the row vectors to get rid of high-frequency spatial noise. Since the lighting of the strip may not always be 100% uniform, the vector is subtracted from its convex hull. Then the highest peak is found and anything less than 10% of it is zeroed out.

Figure 7A:
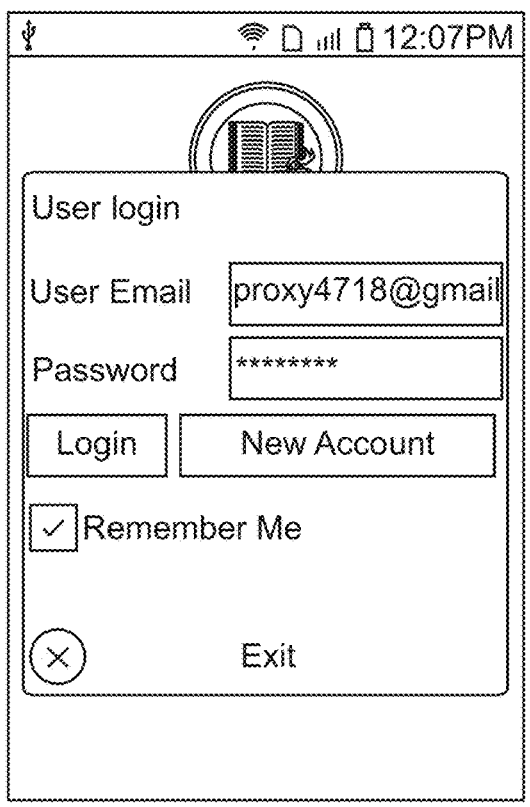
FIG. 7A illustrates a user login screen on a mobile phone that is used to access the RDT application.
Figure 7B:
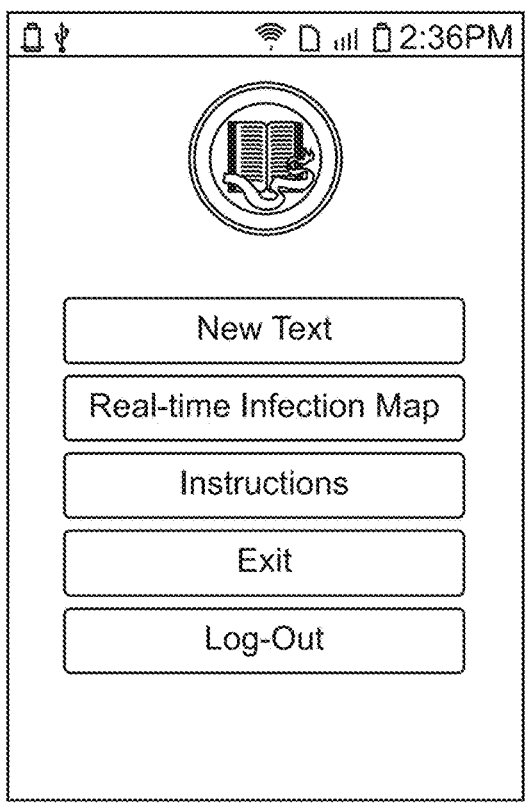
FIG. 7B illustrates an illustrative user menu presented to the user of a mobile phone running the RDT application.
Figure 7C:
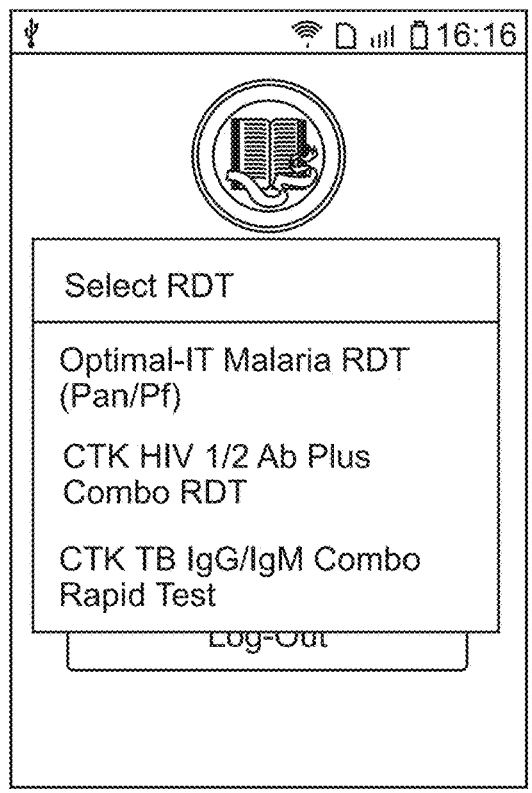
FIG. 7C illustrates an exemplary menu that prompts a user to select from a list of pre-programmed RDTs.

For the final decision, first the presence of a control line is checked at the location where it is presumed to be. If it is present, the test is valid, and otherwise it is labeled as an invalid test. If the test is valid, the locations of the infection-indicating lines are then checked to determine the result of the test (i.e., positive or negative). Note that for different RDT 10 types, from various manufacturers, minor modifications of the above discussed processing flow could be needed to handle variations in the design and packaging of different types of tests FIGS. 7A-7G illustrate various user prompts, input screens, and information that is presented to the user of the system 30 according to one embodiment. As seen in FIG. 7A, the application running on the mobile phone 32 starts with a login screen where the user fills in the form with his or her credentials to thereby create a HTTP POST to the server 90. The server 90 verifies the authenticity of the user and finds the user in the database and returns the necessary cookie files with their user information. The server 90 may run using a MySQL 2 database running RoR or Rails. As seen in FIG. 7B, the user is presented with an application menu where the user can analyze new diagnostic tests, browse through a real-time database of tests (e.g., SQLite) or set the preferences for the application. If the user selects to image a new test, a pull-down menu of pre-configured RDT test is presented to the user and the user can then browse and select the appropriate test kit as seen in FIG. 7C. The software may be updated as new RDTs are developed or become available.

When the user decides on a new test to be evaluated, the mobile phone application accesses and powers on the back facing camera of the phone and the user decides whether they want to turn on the transmission or reflection illumination LED arrays (i.e., first illumination source 60 or second illumination source 62). When the test reader 50 is all the way in the housing 52 (for example, as determined by position sensor 56), the application starts grabbing frames from the camera 34 and displays them on the display 46 of the mobile phone 32. If the user wants to diagnose the RDT 10, the user touches the screen (or other input device such as button) to capture an image of the RDT 10 to be analyzed. FIG. 7D illustrates a raw image taken of the RDT 10.

The digitally captured RDT image is then converted into a grayscale matrix which is analyzed by an identification algorithm such as that illustrated in FIG. 6 to determine the type of test being captured, unless the user has already specified its type. Once the test type is determined, the mobile phone 32 analyses the grayscale matrix for test features (i.e., control and test lines, test bands, test dots, and the like) specific for this particular test type. After extracting and diagnosing test features, the application displays an evaluation form as seen in FIG. 7E including an automatically generated test report (Valid/Invalid and Negative/Positive) as well as patient age, sex, additional comments/information, etc. which can be manually entered. The user can then decide to upload the completed form and the processed image of the RDT 10 to the server 90, or save it onto the mobile phone's local memory for transmission later on. If the results are sent to the server 90, the server 90 checks the credentials of the user and saves the new data into its database.

The user can also reach the real-time RDT monitoring database running on the local server and browse through a global map of previously uploaded test results. The server displays the test data on an internet browser using commercially available mapping applications (e.g., Google Maps) and can filter the data displayed based on several attributes, including: disease type, test location and time/date, RDT type/manufacturer, patient age, etc. The users can access this real-time monitoring platform through the same mobile phone 32 as seen in the mobile phone display image seen in FIG. 7F or using a personal computer 94 (as seen in FIG. 5) with internet connection. The same mobile phone 32 running the application contained thereon can quantify the test line color intensity which can then be correlated to the level of antigen density. That is to say that line color intensity may be correlated with the density of the particular target molecule, protein, and antigen.

Experimental Results

The performance of the mobile phone-based RDT reader was validated by imaging several lateral flow based RDTs including Optimal-IT *P. falciparum*-specific and Pan-specific Malaria Tests (Bio-Rad Laboratories, Inc., CA, USA), HIV 1/2 Ab PLUS Combo Rapid Tests as well as TB IgG/IgM Combo Rapid Tests (CTK Biotech Inc., CA, USA). In order to activate malaria tests, OptiMAL positive control wells (Bio-Rad Laboratories, Inc., CA, USA) were used containing recombinant antigens (LDH) of *P. falciparum*.

Figures 8A, 8B:
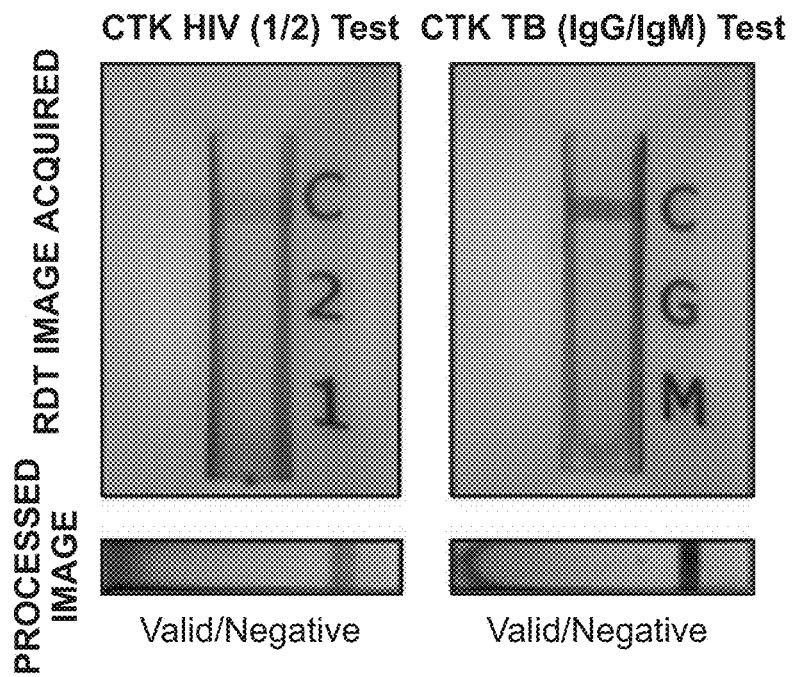
FIG. 8A illustrates the acquired image of the HIV 1/2 Ab PLUS Combo RDT obtained from the camera of a mobile phone. Also illustrated below the raw image is the processed image showing that the sample is valid and negative.
FIG. 8B illustrates the acquired image of the TB (IgG/IgM) RDT obtained from the camera of a mobile phone. Also illustrated below the raw image is the processed image showing that the sample is valid and negative.

Following the manufacturer's instructions, Malaria, HIV and TB RDTs were tested using whole blood samples. Prior to imaging experiments, test results were verified by visual inspection, and the mobile phone-based imaging experiments were repeated more than 10 times in order to validate repeatability of measurements. Although some lateral flow artifacts were visually observed in some cases, the RDT reader application provided the correct results in all tests. FIG. 8A illustrates the raw acquired image of the HIV 1/2 Combo RDT along with digitally processed reflection images of the RFTs which are activated by fresh whole blood samples. Also indicated in FIG. 8A is the automated decisions (e.g., valid/negative) made by the application running on the mobile phone 32. As seen in FIG. 8A, there is a control reagent line indicating the validity of the test, and two pre-deposited antigen (HIV-1 and HIV-2) coated lines indicating the infections. FIG. 8B illustrates the raw acquired image of the TB IgG/IgM Combo RDT along with digitally processed reflection images of the RFTs which are activated by fresh whole blood samples. TB IgG/IgM Combo RDT is also a lateral-flow based immunoassay for simultaneous detection and differentiation of IgM anti-Mycobacterium Tuberculosis (M.TB) and IgG anti-M.TB in human serum or whole blood (shown in raw images as M and G, respectively). Also indicated in FIG. 8B is the automated decisions (e.g., valid/negative) made by the application running on the mobile phone 32. The control line is present with no line at either the M or G row indicating a valid, negative test.

Figures 8C, 8D, 8E:
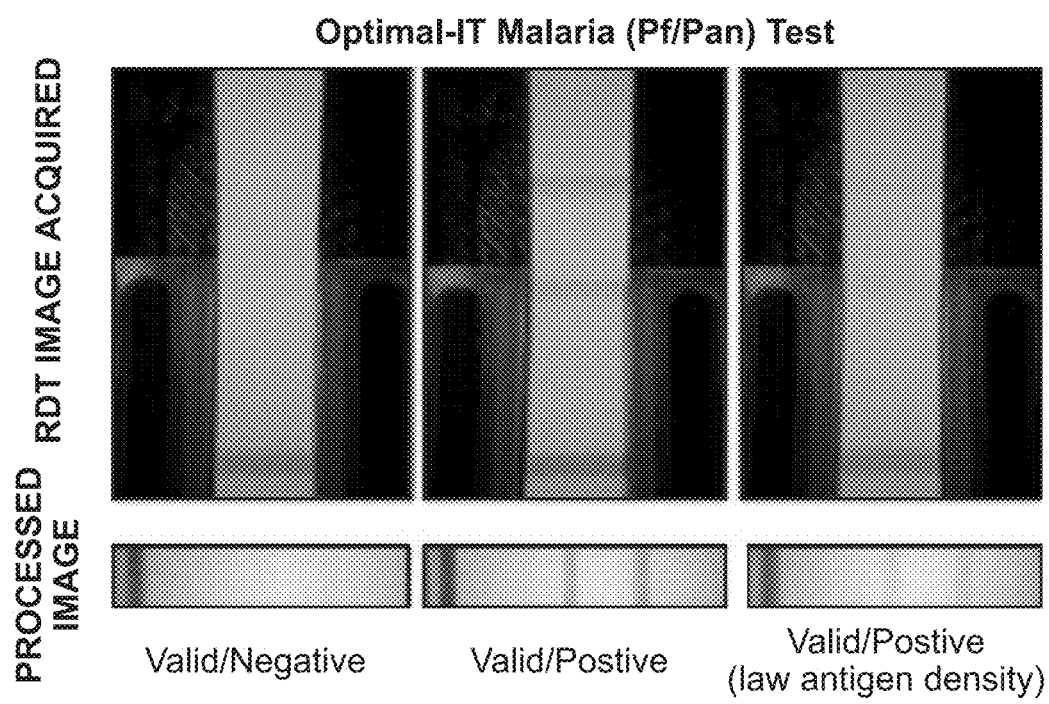
FIG. 8C illustrates the acquired image of the Optimal-IT Malaria (Pf/Pan) RDT obtained from the camera of a mobile phone. Also illustrated below the raw image is the processed image showing that the sample is valid and negative.
FIG. 8D illustrates the acquired image of the Optimal-IT Malaria (Pf/Pan) RDT loaded with a positive sample obtained from the camera of a mobile phone. Also illustrated below the raw image is the processed image showing that the sample is valid and positive (showing two bands in addition to control band).
FIG. 8E illustrates the acquired image of the Optimal-IT Malaria (Pf/Pan) RDT loaded with a highly diluted sample obtained from the camera of a mobile phone. Also illustrated below the raw image is the processed image showing that the sample is valid and positive (showing two feint bands in addition to control band). The feint bands are caused the low antigen density that resulted from the dilution process.

Malaria RDTs were also tested using OptiMAL positive control wells which contain recombinant antigens (LDH) of *P. falciparum*. These tests were activated based on the instructions provided by the manufacturer, and *P. falciparum*-specific as well as Pan-specific (*P. Falciparum, P. Vivax, P. Ovale* and *P. malariae*) reagent lines were clearly observed and evaluated as positive by the RDT application running on the mobile phone. FIGS. 8C-8E illustrate the raw acquired reflection image of the OptiMAL RDT along with digitally processed reflection images of the RFTs which are activated by blood. FIG. 8C illustrates a valid, negative test as evidenced by the presence of the control line but no other test lines that detect Plasmodium antigens (pLDH) using monoclonal antibodies. FIG. 8D illustrates a valid, positive OptiMAL RDT as evidenced by the presence of the control line plus two test lines. In the test of FIG. 8D, positive control wells were used which were previously coated by recombinant antigens of *P. falciparum*.

To further shed light on the performance of the mobile phone-based RDT reader shown, highly diluted positive control samples were imaged and automatically evaluated using Optimal-IT *P. falciparum* and Pan-Malaria RDT. FIG. 8E illustrates valid, positive OptiMAL RDT as evidenced by the presence of the control line plus two feint test lines. This, despite the samples being diluted beyond manufacturer recommendations. Pan-Malaria specific antigens that are previously deposited inside the control wells were released by mixing with sample diluents provided by the manufacturer. The experiments were started with an initial concentration of Positive Control Well Antigen (PCWA)/20 μl, which is the "recommended" dilution level by the manufacturer. Next we diluted it by 2, 3, and 4 times to create lower concentration levels of PCWA/40 μl (2× dilution), PCWA/60 μl (3× dilution), and PCWA/80 μl (4× dilution), respectively.

Figure 9:
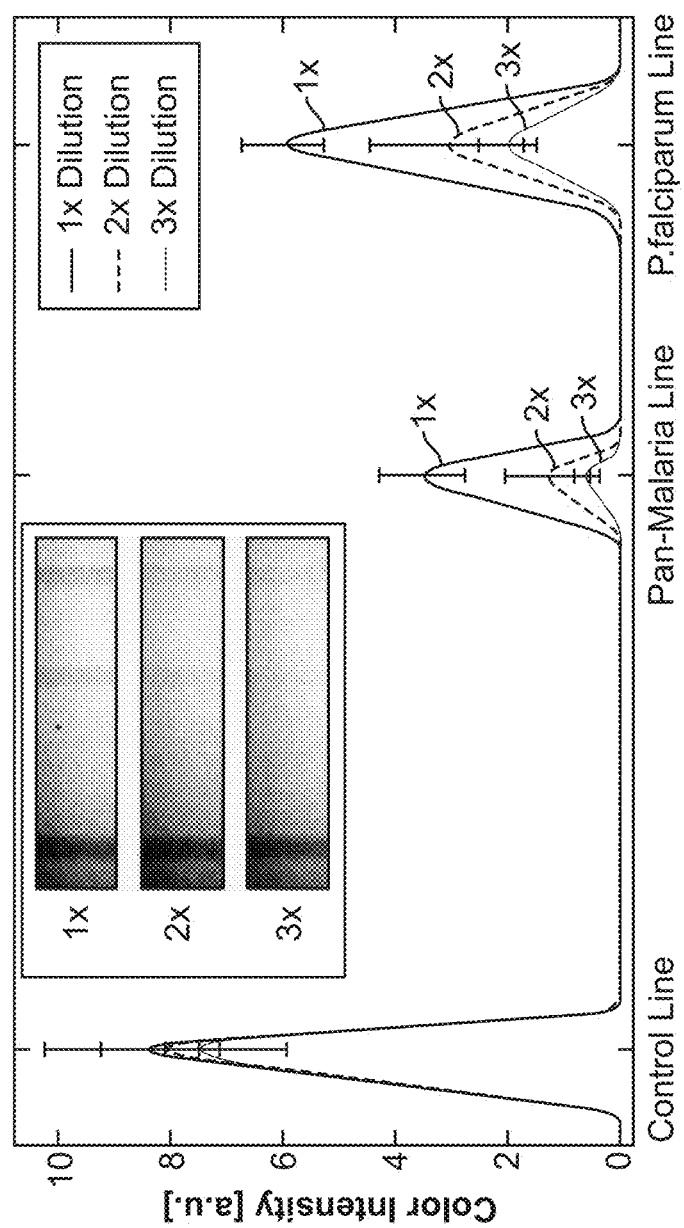
FIG. 9 illustrates a graph of color intensity of a Optimal-IT Malaria (Pf/Pan) RDT test strip subject to varying dilutions levels (1×, 2×, and 3×). Inset in the graph are respective strip test images of the various dilution tests.

Ten (10) RDT measurements for each one of these concentration levels (i.e., 40 measurements total) were made. In these experiments, the mobile phone platform correctly analyzed (yielding valid & positive results) all the Malaria RDTs that were activated with PCWA/20 μl, PCWA/40 μl as well as PCWA/60 μl. However, the accuracy decreased to ~60% for PCWA/80 μl (i.e., at 4× lower concentration compared to the suggested dilution level) which is due to the low antigen density and the corresponding weak color intensity. FIG. 9 illustrates the average cross-sectional intensity profiles of these RDT strips for PCWA/20 μl, PCWA/40 μl as well as PCWA/60 μl. In these results, it is important to emphasize that the cross-sectional intensity of the control line has no correlation with the density of the malaria antigens as it indicates only the validity of the RDT. On the other hand, a higher average intensity on *P. Falciparum* infection line was observed as compared to the average intensity of the Pan-Malaria infection line for all the concentration levels. This is expected since *P. Falciparum* lines were pre-deposited by only *P. Falciparum* specific antibodies, whereas Pan-malaria lines are specific to all four kinds of *Plasmodium* (Malaria) species (*P. falciparum, P.vivax, P.ovale* and *P.malariae*), exhibiting weaker response compared to the *P. Falciparum* test line. These results highlight the sensitivity of the platform to differentiate such minor variations (in response to analytes) which are quite difficult to observe and quantify during visual examination of RDTs by humans, especially under varying illumination and imaging conditions that might occur in field conditions.

While embodiments have been shown and described, various modifications may be made without departing from the scope of the inventive concepts disclosed herein. The invention(s), therefore, should not be limited, except to the following claims, and their equivalents.

What is claimed is:

1. A method of reading a rapid diagnostic test loaded with a sample using a mobile phone or other portable electronic device having camera functionality comprising:

removably securing a separate hand-held rapid diagnostic test reader to the mobile phone or other portable electronic device, the rapid diagnostic test reader weighing less than 300 grams and including both a transmission illumination source and a reflection illumination source;

inserting the rapid diagnostic test into the reader, the rapid diagnostic test comprising a test location and a control location;

selecting one of the transmission illumination source and the reflection illumination source;

illuminating the rapid diagnostic test with illumination from the selected illumination source;

capturing an image of the test location and control location with the camera of the mobile phone or other portable electronic device; and processing the captured image with image processing software executed by at least one processor, the image processing software converting the captured image to grayscale and extracting regions of interest from the test location and the control location in the grayscale image of the field of view, the image processing software and compares respective measured intensity values of the regions of interest with respective intensity threshold values and outputting a test result for the sample to the user based at least in part on the comparisons, the test result comprising a positive/negative indication as well as a validity indication.

2. The method of claim 1, wherein the captured image is processed using one or more processors contained in the mobile phone or other portable electronic device.

3. The method of claim 1, further comprising transferring the test result to a database at a remote location.

4. The method of claim 1, wherein the captured image is transmitted to a remote location using an application or software program running on the mobile phone or other portable electronic device and wherein said processing occurs at the remote location.

5. The method of claim 4, further comprising returning the test result(s) to the application or software program running on the mobile phone or other portable electronic device via wireless telecommunication.

6. The method of claim 1, further comprising transmitting the captured image along with a test report to a remote computer.

7. The method of claim 6, wherein the test report comprises a test validity indication, image data, and user-input data.

8. The method of claim 7, wherein the test report comprises geographical location and time-stamp data.

9. The method of claim 6, further comprising querying of test results a remotely located database connected to the remote computer, the database containing a plurality of test results, and returning a response to the user submitting the query from the remote computer.

10. The method of claim 9, wherein the query is submitted from an application or software program on the mobile phone or other portable electronic device.

11. The method of claim 9, wherein the query is submitted from a computer.

12. A method of claim 9, wherein the returned response is received by an application or software running on the mobile phone or other portable electronic device comprises a plurality of rapid diagnostic test results of a pathological condition over at least one of an extended geographical area or time period.

13. The method of claim 12, wherein the rapid diagnostic test results comprise data corresponding to quantification of response, detection, or sensing level.

14. The method of claim 12, wherein the rapid diagnostic test results comprise an image.

* * * * *